United States Patent
Sharratt et al.

(10) Patent No.: US 11,352,313 B2
(45) Date of Patent: Jun. 7, 2022

(54) FLUORINATED DIESTER COMPOUNDS AND THEIR USE IN HEAT TRANSFER SYSTEM

(71) Applicant: MEXICHEM FLUOR S.A. DE C.V., San Luis Potosi C.P. (MX)

(72) Inventors: Andrew Paul Sharratt, Runcorn (GB); Robert Elliott Low, Runcorn (GB); Emma Jane Hodgson, Runcorn (GB)

(*) Notice: Subject to any disclaimer, the term of this patent is extended or adjusted under 35 U.S.C. 154(b) by 0 days.

(21) Appl. No.: 16/794,881

(22) Filed: Feb. 19, 2020

(65) Prior Publication Data
US 2020/0239403 A1    Jul. 30, 2020

Related U.S. Application Data

(63) Continuation of application No. 15/520,774, filed as application No. PCT/GB2015/053148 on Oct. 21, 2015, now Pat. No. 10,766,849.

(30) Foreign Application Priority Data

Oct. 21, 2014 (GB) .................................... 1418709

(51) Int. Cl.
| | |
|---|---|
| C07C 69/63 | (2006.01) |
| C09K 5/04 | (2006.01) |
| C10M 171/00 | (2006.01) |
| C10M 105/54 | (2006.01) |
| C07C 67/14 | (2006.01) |
| C10M 105/18 | (2006.01) |
| C10M 105/38 | (2006.01) |
| C10N 10/06 | (2006.01) |
| C10N 10/10 | (2006.01) |
| C10N 20/00 | (2006.01) |
| C10N 30/08 | (2006.01) |
| C10N 40/30 | (2006.01) |
| C10N 30/00 | (2006.01) |

(52) U.S. Cl.
CPC .............. *C07C 69/63* (2013.01); *C07C 67/14* (2013.01); *C09K 5/045* (2013.01); *C10M 105/18* (2013.01); *C10M 105/38* (2013.01); *C10M 105/54* (2013.01); *C10M 171/008* (2013.01); *C09K 2205/104* (2013.01); *C10M 2201/085* (2013.01); *C10M 2207/0406* (2013.01); *C10M 2207/2835* (2013.01); *C10M 2211/022* (2013.01); *C10M 2211/0445* (2013.01); *C10M 2211/06* (2013.01); *C10M 2223/04* (2013.01); *C10M 2223/043* (2013.01); *C10N 2010/06* (2013.01); *C10N 2010/10* (2013.01); *C10N 2020/099* (2020.05); *C10N 2020/101* (2020.05); *C10N 2020/103* (2020.05); *C10N 2020/106* (2020.05); *C10N 2030/08* (2013.01); *C10N 2030/50* (2020.05); *C10N 2030/54* (2020.05); *C10N 2030/64* (2020.05); *C10N 2030/66* (2020.05); *C10N 2040/30* (2013.01)

(58) Field of Classification Search
CPC ....................................................... C07C 69/63
See application file for complete search history.

(56) References Cited

U.S. PATENT DOCUMENTS

| | | | |
|---|---|---|---|
| 3,210,404 A | | 10/1965 | Durr et al. |
| 3,262,881 A | * | 7/1966 | Ravner .................. C07C 69/34 |
| | | | 508/498 |
| 2016/0333245 A1 | * | 11/2016 | Fujii ...................... C09K 5/045 |

FOREIGN PATENT DOCUMENTS

| | | |
|---|---|---|
| CN | 102732357 A | 10/2012 |
| EP | 0440069 A1 | 8/1991 |
| EP | 0536940 A2 | 4/1993 |
| GB | 1 244 841 | 9/1971 |
| GB | 1 266 408 | 3/1972 |
| JP | 63-045237 A | 2/1988 |
| SU | 533131 A1 | 6/1985 |
| WO | WO0065002 A1 | 11/2000 |
| WO | WO 2007/082046 A1 | 7/2007 |

OTHER PUBLICATIONS

Durr Jr et al., Preprints General Papers Division of Petroleum Chemistry, "Diesters with Improved Thermal and Hydrolytic Stability", vol. 8, No. 3, (1963), pp. 49-56.
Robert Filler et al: "Diesters of Carboxylic Acids With Fluorinated Alcohols and Glycols", J.A.C.S. 1953, 75, Jun. 5, 1953 (Jun. 5, 1953), pp. 2693-2695.
Robert Filler et al: "Properties of Fluorine-Containing Diesters—Correlative Studies", Industrial and Engineering Chemistry, 1954, 46, Jan. 1, 1954 (Jan. 1, 1954), pp. 544-547.
P. D. Faurote et al: "Partially Fluorinated Esters and Ethers as Temperature-Stable Liquids", Industrial & Engineering Chemistry, vol. 48, No. 3, Mar. 1, 1956 (Mar. 1, 1956), pp. 445-454.
Kenneth N. Marsh et al: "Review of thermodynamic properties of refrigerants + Tubricant oils", Fluid Phase Equilibria, vol. 199, No. 1-2, Jun. 1, 2002 (Jun. 1, 2002), pp. 319-334.
Youbi-Idrissi et al: "The effect of oil in refrigeration: Current research issues and critical review of thermodynamic aspects", International Journal of Refrigeration, Elsevier, Paris, FR, vol. 31, No. 2, Feb. 26, 2008 (Feb. 26, 2008), pp. 165-179.
International Search Report and Written Opinion in PCT Application No. PCT/GB2015/053148, dated Apr. 28, 2016, 12 pages.

* cited by examiner

*Primary Examiner* — William D Young
(74) *Attorney, Agent, or Firm* — Yuezhong Feng; Crowell & Moring LLP

(57) ABSTRACT

A compound of formula (I): wherein W is independently selected from the group consisting of H, F, Cl, Br, and I; X is independently selected from the group consisting of H, F, Cl, Br, and I; Y is independently selected from the group consisting of F, Cl, Br, and I; Z is independently selected from the group consisting of H, F, Cl, Br, and I; n is an integer from 1 to 8; and n' is an integer from 1 to 12.

(I)

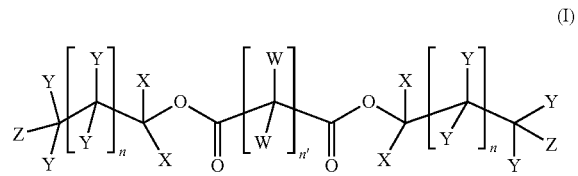

11 Claims, 1 Drawing Sheet

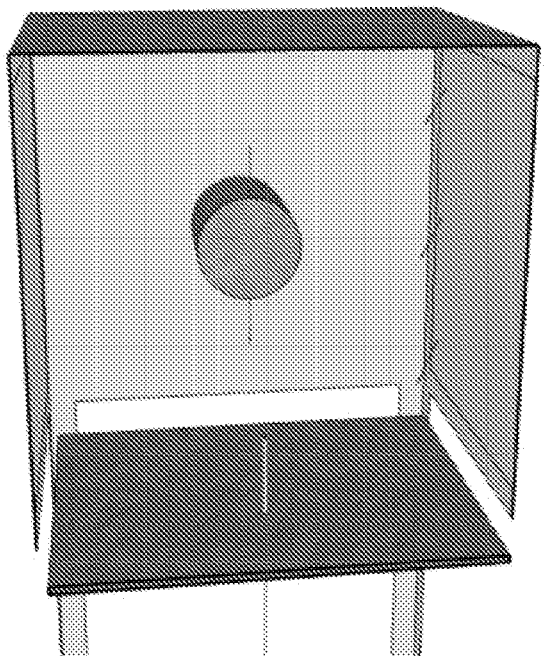

FLUORINATED DIESTER COMPOUNDS AND THEIR USE IN HEAT TRANSFER SYSTEM

This application is a continuation application of U.S. patent application Ser. No. 15/520,774, filed Apr. 20, 2017, which is the U.S. National Phase under 35 U.S.C. § 371 of International Application No. PCT/GB2015/053148, filed Oct. 21, 2015, designating the United States and published in English on Apr. 28, 2016, as WO 2016/063056, which claims priority to United Kingdom Application No. 1418709.0, filed Oct. 21, 2014, each of which is incorporated by reference herein in its entirety.

FIELD

The present invention relates to diester compounds and to uses of and methods of preparing the same.

BACKGROUND

The listing or discussion of information or a prior-published document in this specification should not necessarily be taken as an acknowledgement that the information or document is part of the state of the art or is common general knowledge.

Fluorocarbon-based compounds are currently used in a large number of commercial and industrial applications, such as propellants, blowing agents and heat transfer fluids. The interest in and use of fluorine-based compounds, particularly (hydro)fluoroolefins, as heat transfer fluids has increased as new refrigerants are sought.

Dichlorodifluoromethane (refrigerant R-12) possessed a suitable combination of refrigerant properties and was for many years the most widely used refrigerant. Due to international concern that fully and partially halogenated chlorofluorocarbons, such as dichlorodifluoromethane and chlorodifluoromethane, were damaging the earth's protective ozone layer, there was general agreement that their manufacture and use should be severely restricted and eventually phased out completely. The use of dichlorodifluoromethane was phased out in the 1990's.

Chlorodifluoromethane (R-22) was introduced as a replacement for R-12 because of its lower ozone depletion potential. Following concerns that R-22 is a potent greenhouse gas, its use is also being phased out. R-410A and R-407 (including R-407A, R-407B and R-407C) have been introduced as a replacement refrigerant for R-22. However, R-22, R-410A and the R-407 refrigerants all have a high global warming potential (GWP, also known as greenhouse warming potential).

1,1,1,2-tetrafluoroethane (refrigerant R-134a) was introduced as a replacement refrigerant for R-12. However, despite having a low ozone depletion potential, R-134a has a GWP of 1430. It would be desirable to find replacements for R-134a that have a lower GWP.

R-152a (1,1-difluoroethane) has been identified as an alternative to R-134a. It is somewhat more efficient than R-134a and has a greenhouse warming potential of 120. However the flammability of R-152a is judged too high, for example to permit its safe use in mobile air conditioning systems. In particular its lower flammable limit in air is too low, its flame speeds are too high, and its ignition energy is too low.

(Hydro)fluoroolefins, particularly tetrafluoropropenes, have been proposed as a possible refrigerants for use in a variety of heat transfer devices.

Heat transfer fluids are often used in combination with lubricants, such as in heating and refrigeration systems. Such lubricants are included in heat transfer compositions to ensure continued smooth operation of the heat transfer system.

It is necessary that lubricants used in heat transfer compositions are compatible with the refrigerants in the compositions. The compatibility of the lubricant and the refrigerant is predicated on a number of factors, such as a desire for at least partial miscibility at part of the operating temperature range, a low tendency to degrade or react in use and appropriate viscosities for the application.

There is therefore a need for lubricants that can be used in conjunction with heat transfer fluids, both those currently used and those proposed as replacement compositions. In particular, lubricants are desired that are miscible with a wide range of heat transfer fluids, possess an appropriate viscosity, do not reduce the performance of heat transfer fluids and have low flammability; all in addition to successfully functioning as a lubricant.

Lubricants with low flammability are particularly important for heat transfer fluids that are used in automobile air-conditioning, as such compositions are in danger of coming into contact with hot metal surfaces of the engine.

SUMMARY

The subject invention addresses the above and other deficiencies by the provision of a compound of formula (I):

$$\text{Formula (I)}$$

wherein

W is independently selected from the group consisting of H, F, Cl, Br, and I;

X is independently selected from the group consisting of H, F, Cl, Br, and I;

Y is independently selected from the group consisting of F, Cl, Br, and I;

Z is independently selected from the group consisting of H, F, Cl, Br, and I;

n is an integer from 1 to 8;

and n' is an integer from 1 to 12.

Also provided by the invention is a composition comprising a heat transfer fluid, together with one or more compounds of formula (I).

Further provided by the invention is a method of preparing a compound of formula (I) comprising reacting a compound of formula (A) with a compound of formula (B):

$$\text{Formula (A)}$$

-continued

Formula (B)

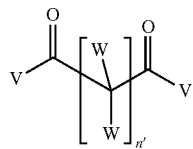

wherein

W is independently selected from the group consisting of H, F, Cl, Br, and I;

X is independently selected from the group consisting of H, F, Cl, Br, and I;

Y is independently selected from the group consisting of F, Cl, Br, and I;

Z is independently selected from the group consisting of H, F, Cl, Br, and I;

V is independently selected from the group consisting of Cl and OH;

n is an integer from 1 to 8;

and n' is an integer from 1 to 12.

DETAILED DESCRIPTION

Compounds of the Invention

In one aspect, the invention provides a compound of formula (I):

Formula (I)

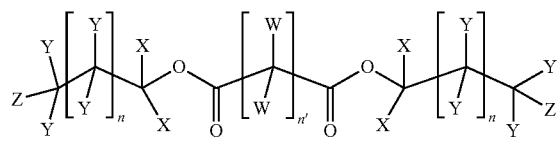

wherein

W is independently selected from the group consisting of H, F, Cl, Br, and I;

X is independently selected from the group consisting of H, F, Cl, Br, and I;

Y is independently selected from the group consisting of F, Cl, Br, and I;

Z is independently selected from the group consisting of H, F, Cl, Br, and I;

n is an integer from 1 to 8;

and n' is an integer from 1 to 12.

In an embodiment, W and X are independently H or F, preferably H. Preferably, Y is F. Preferably, Z is H or F. Advantageously, n is an integer from 1 to 5, for example, an integer from 2 to 5. Preferably, n' is an integer from 1 to 10, for example, an integer from 2 to 8, e.g. 3, 4, 5 or 6.

In an embodiment of the invention, the compound of formula (I) is a compound of formula (II):

Formula (II)

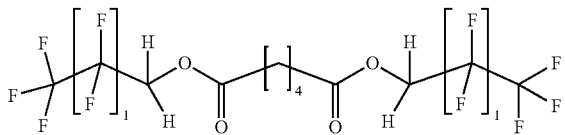

In a further embodiment of the invention, the compound of formula (I) is a compound of formula (III)

Formula (III)

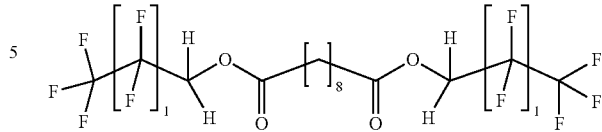

In an alternative embodiment of the invention, the compound of formula (I) is a compound of formula (IV)

Formula (IV)

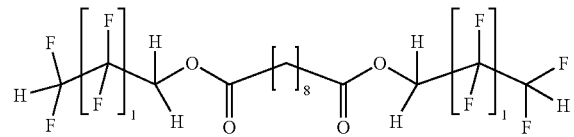

In an embodiment of the invention, there is a provided a composition comprising at least two different compounds of formula (I).

In an embodiment, the value of n is the same for the at least two compounds of formula (I). Alternatively, the values of n for the at least two compounds of formula (I) are different.

In an embodiment, the value of n' is the same for the at least two compounds of formula (I). Alternatively, the values of n' for the at least two compounds of formula (I) are different, such as one value of n' being twice that of the other.

In an embodiment, the identity of X, Y or Z may be the same or different for the at least two compounds of formula (I). Preferably, the identity of Z may both be H, both be F, or may be H for one of the compounds of formula (I) and F for another compound of Formula (I).

In a further embodiment, there is a provided a composition comprising at least two compounds of formula (I), wherein at least one compound of formula (I) is a compound of formula (V) and at least one compound of formula (I) is a compound of formula (VI).

Formula (V)

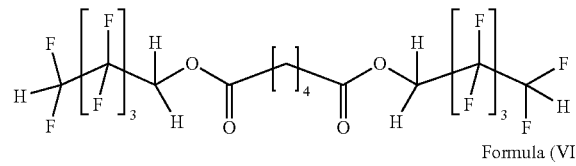

Formula (VI)

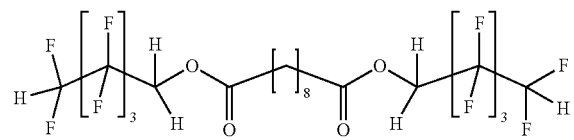

The compounds of formula (I) are less flammable than polyalkylene glycol (PAG) and/or polyol ester (POE) based lubricants. Preferably, the compounds of formula (I) have a lowest temperature of ignition of about 500° C. or greater, such as 510° C., 520° C., 530° C., 540° C., 550° C., 560° C., 570° C., 580° C., 590° C., preferably about 600° C. or greater, for example 610° C., 620° C., 630° C. or 640° C.

Advantageously, the compounds of formula have a high degree of miscibility with heat transfer fluids, particularly fluorine-based heat transfer fluids.

Preferably, the compounds of formula (I) will have a melting point of from about −20° C. to about −70° C., such as from about −25° C. to about −60° C., preferably from about −30° C. to about −50° C.

Preferably, the compounds of formula (I) will have a viscosity appropriate for use with heat transfer fluids, such as in refrigeration or air-conditioning devices. Conveniently, compounds of formula (I) with have a viscosity of from about 20 to about 70 cSt, such as from 25 to about 65 cSt, from about 30 to about 60 cSt or from about 35 to about 55 cSt. Preferably, the compounds of formula (I) will have a viscosity of from about 40 to about 50 cSt.

The compounds of formula (I) may be further used as heat transfer agents.

Compositions of the Invention

In another aspect, the invention provides a composition comprising a heat transfer fluid, together with one or more compounds of formula (I).

In an embodiment, the composition may comprise a heat transfer fluid and one or more compounds of formula (II), (III) or (IV). Alternatively or additionally the composition may comprise at least two compounds of formula (I), for example, wherein at least one compound of formula (I) is a compound of formula (V) and at least one compound of formula (I) is a compound of formula (VI).

In an alternative embodiment, the composition may comprise a heat transfer fluid and a compound of formula (VII).

Formula (VII)

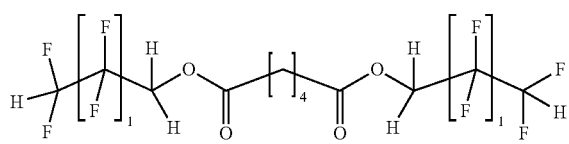

Preferably, the heat transfer fluid comprises one or more compounds selected from the group of (hydro)fluoroolefins (HFOs), hydrofluorocarbons (HFCs), chlorofluorocarbons (CFCs), hydrochlorofluorocarbons (HCFCs) and hydrocarbons.

Advantageously, the heat transfer fluid may comprise one or more compounds selected from the group of 1,3,3,3-tetrafluoropropene (R-1234ze), 2,3,3,3-tetrafluoropropene (R-1234yf), 3,3,3-trifluoropropene (R-1243zf), 1,1,1-trifluoro-2-chloropropene (R-1233xf), 1,1,1-trifluoro-3-chloropropene (R-1233zd), 1,1,1,2-tetrafluoroethane (R-134a), 1,1-difluoroethane (R-152a), difluoromethane (R-32), fluoroethane (R-161), pentafluoroethane (R-125), 1,1,2,2-tetrafluoroethane (R-134), propane, propylene, carbon dioxide, 1,1,1,3,3-pentafluoropropane (R-245fa), 1,1,1,3,3,3-hexofluoropropane (R-236fa), 1,1,1,2,3,3,3-heptafluoropropane (R-227ea), 1,1,1-trifluoroethane (R-143a), n-butane, iso-butane and 1,1,1,3,3-pentafluorobutane (R-365mfc), such as R-1234ze, R-1234yf, R-1243zf, R-134a, R-152a and R-32.

For the avoidance of doubt, it is to be understood that where a compound may exist as one of two configurational isomers, e.g. cis and trans isomers around a double bond, the use of the term without an isomer designation (e.g. R-1234ze or R-1233zd) is to refer to either isomer.

In some embodiments, the heat transfer fluid comprises tetrafluoropropenes. Preferably, the heat transfer fluid comprises R-1234ze, even more preferably the heat transfer fluid comprises R-1234ze(E). Advantageously, the heat transfer composition comprises R-1234yf.

Advantageously, compositions of the invention are less flammable than a composition comprising the same heat transfer fluid combined with a polyalkylene glycol (PAG) and/or a polyol ester (POE) based lubricant.

Preferably, the compositions of the invention are less flammable than the heat transfer fluid alone.

Preferably, the composition of the invention has a lowest temperature of ignition of about 500° C. or greater, such as 510° C., 520° C., 530° C., 540° C., 550° C., 560° C., 570° C., 580° C., 590° C., preferably about 600° C. or greater, for example 610° C., 620° C., 630° C. or 640° C.

In an embodiment, the composition of the invention may be non-flammable.

Flammability may be determined in accordance with ASHRAE Standard 34 incorporating the ASTM Standard E-681 with test methodology as per Addendum 34p dated 2004, the entire content of which is incorporated herein by reference.

Conveniently, the Global Warming Potential (GWP) of the compositions of the invention may be less than about 3500, 3000, 2500 or 2000. For instance, the GWP may be less than 2500, 2400, 2300, 2200, 2100, 2000, 1900, 1800, 1700, 1600 or 1500. The GWP of the compositions of the invention preferably is less than 1400, 1300, 1200, 1100, 1000, 900, 800, 700, 600 or 500.

Preferably, the compositions of the invention have zero or near zero ozone depletion.

In an embodiment, the compositions of the invention have improved heat transfer properties than the heat transfer fluid alone.

Without wishing to be bound by theory, it is believed that compounds of formula (I) may further act as heat transfer agents and therefore increase the heat transfer properties of the compositions of the invention.

Advantageously, the composition further comprises a stabiliser.

Preferably the stabiliser is selected from group consisting of diene-based compounds, phosphates, phenol compounds and epoxides, and mixtures thereof.

Conveniently, the composition further comprises an additional flame retardant.

Preferably, the flame retardant is selected from the group consisting of tri-(2-chloroethyl)-phosphate, (chloropropyl) phosphate, tri-(2,3-dibromopropyl)-phosphate, tri-(1,3-dichloropropyl)-phosphate, diammonium phosphate, various halogenated aromatic compounds, antimony oxide, aluminium trihydrate, polyvinyl chloride, a fluorinated iodocarbon, a fluorinated bromocarbon, trifluoro iodomethane, perfluoroalkyl amines, bromo-fluoroalkyl amines and mixtures thereof.

The invention also provides a heat transfer device containing a composition of the invention and/or the use of a composition of the invention in a heat transfer device.

In an embodiment, the heat transfer device is a refrigeration device.

Conveniently, the heat transfer device is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

Preferably, the heat transfer device contains a compressor.

According to a further aspect of the invention, there is provided a method of cooling an article, which comprises condensing a composition of the invention and thereafter evaporating the composition in the vicinity of the article to be cooled.

According to an another aspect of the invention, there is provided a method for heating an article, which comprises condensing a composition of the invention in the vicinity of the article to be heated and thereafter evaporating the composition.

According to a further aspect of the invention, there is provided a mechanical power generation device containing a composition of the invention.

Preferably, the mechanical power generating device is adapted to use a Rankine Cycle or modification thereof to generate work from heat.

According to an another aspect of the invention, there is provided a method of retrofitting a heat transfer device comprising the step of removing an existing heat transfer fluid and introducing a composition of the invention. Preferably, the heat transfer device is a refrigeration device. Advantageously, the heat transfer device is an air-conditioning system.

According to a further aspect of the invention, there is provided a method of reducing the flammability of a composition by the addition of one or more compounds of formula (I) to (VI).

Methods of Preparation of Compounds and Compositions of the Invention

The invention provides a method of preparing a compound of formula (I) comprising reacting a compound of formula (A) with a compound of formula (B):

Formula (A)

Formula (B)

wherein

W is independently selected from the group consisting of H, F, Cl, Br, and I;

X is independently selected from the group consisting of H, F, Cl, Br, and I;

Y is independently selected from the group consisting of F, Cl, Br, and I;

Z is independently selected from the group consisting of H, F, Cl, Br, or I;

V is independently selected from the group consisting of Cl and OH;

n is an integer from 1 to 8;

and n' is an integer from 1 to 12.

In an embodiment W and X are independently H or F, preferably H. Preferably, Y is F. Preferably, Z is H or F. Conveniently, V is Cl. Advantageously, n is an integer from 1 to 5. Preferably, n' is an integer from 1 to 10, e.g. an integer from 2 to 8 such as 3, 4, 5 or 6.

Preferably, the molar ratio of compound of formula (A) to compound of formula (B) is at least 2:1.

In an aspect of the invention, there is a method of preparing a compound of formula (II) comprising reacting pentafluoropropan-1-ol with a compound of formula (B), wherein n' 4 and W is OH or Cl, preferably wherein W is Cl.

Advantageously, the molar ratio of pentafluoropropan-1-ol to compound of formula (B) is at least 2:1.

In an aspect of the invention, there is a method of preparing a compound of formula (III) comprising reacting pentafluoropropan-1-ol with a compound of formula (B), wherein n' 8 and W is OH or Cl, preferably wherein W is Cl.

Advantageously, the molar ratio of pentafluoropropan-1-ol to compound of formula (B) is at least 2:1.

In an aspect of the invention, there is a method of preparing a compound of formula (IV) comprising reacting 2,2,3,3-tetafluoropropan-1-ol with a compound of formula (B), wherein n' is 8 and W is OH or Cl, preferably wherein W is Cl.

Advantageously, the molar ratio of 2,2,3,3-tetafluoropropan-1-ol to compound of formula (B) is at least 2:1.

In an aspect of the invention, there is a method of preparing a composition comprising at least two compounds of formula (I) wherein at least one compound of formula (I) is a compound of formula (V) and at least one compound of formula (I) is a compound of formula (VI), which method comprises reacting 2,2,3,3,4,4,5,5-octofluoropentan-1-ol with a compound of formula (B'), wherein n' is 4 and W is OH or Cl; and comprising reacting 2,2,3,3,4,4,5,5-octofluoropentan-1-ol with a compound of formula (B"), wherein n' is 8 and W is OH or Cl, preferably wherein W is Cl.

In some embodiments, the method is conducted in one-step reaction. Advantageously, the molar ratio of 2,2,3,3,4,4,5,5-octofluoropentan-1-ol to the combined amount of compounds of formula B' and B" is at least 2:1.

Compositions of the invention may be prepared by the method of mixing one or more compounds of formula (I) to (VI) with a heat transfer fluid.

Composition of the invention may be prepared by mixing one or more compounds or formula (I), prepared through a method of the invention, with a heat transfer fluid.

Preferably, the heat transfer fluid comprises one or more compounds selected from the group of (hydro)fluoroolefins (HFOs), hydrofluorocarbons (HFCs), chlorofluorocarbons (CFCs), hydrochlorofluorocarbons (HCFCs) and hydrocarbons.

Advantageously, the heat transfer fluid comprises one or more compounds selected from the group of R-1234ze, R-1234yf, R-1233xf, R-1233zd, R-1243zf, R-134a, R-152a, R-32, R-161, R-125, R-134, propane, propylene, carbon dioxide, R-245fa, R-236fa, R-227ea, R-143a, n-butane, isobutane and R-365mfc.

Conveniently, wherein the heat transfer fluid comprises one or more compounds selected from the group of R-1234ze, R-1234yf, R-1233xf, R1233zd, R-1243zf, R-134a, R-152a and R-32.

Preferably, the heat transfer fluid comprises R-1234ze.
Preferably, the heat transfer fluid comprises R-1234yf.

EXAMPLES

Synthesis of Compound of Formula (II)

Formula (II)

2,2,3,3,3-pentafluoropropan-1-ol (110 g, 0.73 mol) was charged to a 250 mL round bottom flask fitted with a condenser and dropping funnel. The alcohol was stirred and heated to 40° C. Adipoyl chloride (44.6 g, 0.24 mol) was charged to a dropping funnel and added slowly to the alcohol. The mixture was stirred at 40° C. for approximately 4 to 5 hours, allowed to cool to room temperature and then the excess alcohol was removed under vacuum. The remaining clear oil was filtered to remove particulates and then dried over activated molecular sieves. The reaction gave 78.5 g (78.5% yield) of a compound of Formula (II).

$^1$H NMR (DMSO): δ 4.74-4.83 (t CH$_2$), δ 2.41-2.47 (m C$_2$H$_4$), δ 1.53-1.62 (m C$_2$H$_4$)

$^{13}$C NMR (DMSO): δ 171.21 (s OC=O), δ 120.05 (t CF$_2$), δ 116.26 (t CF$_2$), δ 115.39-112.02 (m CF$_3$), δ 57.79-58.71 (t CH$_2$O), δ 32.35-32.51 (d C$\underline{H}_2$C=O), δ 23.28-23.62 (d CH$_2$)

$^{19}$F NMR (DMSO): δ −6.17−−5.49 (s 6F), δ −47.37−−45.47 (s 4F)

IR: 1764 cm$^{-1}$ (OC=O), 1197 cm$^{-1}$ (C—O), 1137 cm$^{-1}$ (C—F)

TGA: One mass loss is seen giving a boiling range of 240-260° C. No impurities

Density: 1.42 g/ml
Viscosity: 7.06 cP

| RPM | Centipoise (cP) | Torque (%) |
|---|---|---|
| <10 | Out of Range | Out of Range |
| 10 | 6.6 | 11 |
| 12 | 6.6 | 13.2 |
| 20 | 6.78 | 22.6 |
| 30 | 6.94 | 34.7 |
| 50 | 7.02 | 58.5 |
| 60 | 7.06 | 70.6 |
| 100 | Out of Range | Out of Range |

Synthesis of Compound of Formula (III)

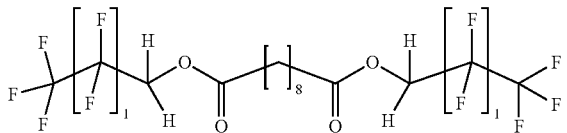

Formula (III)

2,2,3,3,3-pentafluoropropan-1-ol (96.6 g, 0.64 mol) was charged to a 250 mL round bottom flask fitted with a condenser and dropping funnel. The alcohol was stirred and heated to 40° C. Sebacoyl chloride (51.3 g, 0.21 mol) was charged to a dropping funnel and added slowly to the alcohol. The mixture was stirred at 40° C. for approximately 4 to 5 hours, allowed to cool to room temperature and then the excess alcohol was removed under vacuum. The remaining clear oil was filtered to remove particulates and then dried over activated molecular sieves. The reaction gave 40.9 g (40.9% yield) of a compound of Formula (III). The yield is lower than expected due to inadvertent loss of product before weighing.

$^1$H NMR (DMSO): δ 4.73-4.82 (t CH$_2$), δ 2.37-2.42 (t C$_2$H$_4$), δ 1.50-1.55 (m C$_2$H$_4$), δ 1.24 (s C$_4$H$_8$)

$^{13}$C NMR (DMSO): δ 171.43 (s OC=O), δ 120.06 (t CF$_2$), δ 108.69-116.27 (m CF$_3$), δ 57.74-58.46 (t CH$_2$O), δ 32.77 (s C$\underline{H}_2$C=O), δ 27.97-28.44 (m C$_2$H$_4$), δ 24.02-24.36 (d C$_2$H$_4$)

$^{19}$F NMR (DMSO): δ −8.98−−8.29 (s 6F), δ −48.29 (s 4F)

IR: 1764 cm$^{-1}$ (OC=O), 1197 cm$^{-1}$ (C—O), 1149 cm$^{-1}$ (C—F)

TGA: One mass loss is seen giving a boiling range of 280-310° C. No impurities

Density: 1.31 g/ml
Viscosity: 10.51 cP

| RPM | Centipoise (cP) | Torque (%) |
|---|---|---|
| <10 | Out of Range | Out of Range |
| 10 | 10.08 | 16.8 |
| 12 | 10.10 | 20.2 |
| 20 | 10.26 | 34.2 |
| 30 | 10.40 | 52.0 |
| 50 | 10.51 | 87.6 |
| 60 | Out of Range | Out of Range |

Synthesis of Compound of Formula (IV)

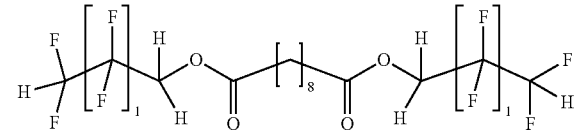

Formula (IV)

2,2,3,3-tetrafluoropropan-1-ol (82.88 g, 0.63 mol) was charged to a 250 mL round bottom flask fitted with a condenser and dropping funnel. The alcohol was stirred and heated to 40° C. Sebacoyl chloride (50.05 g, 0.21 mol) was charged to a dropping funnel and added slowly to the alcohol. The mixture was stirred at 40° C. for approximately 4 to 5 hours, allowed to cool to room temperature and then the excess alcohol was removed under vacuum. The remaining clear oil was filtered to remove particulates and then dried over activated molecular sieves. The reaction gave 60 g (67% yield) of a compound of Formula (IV).

$^1$H NMR (DMSO): δ 6.38-6.77 (tt, CF$_2$H), δ 4.53-4.63 (t CH$_2$), δ 2.37-2.42 (t C$_2$H$_4$), δ 1.51-1.56 (m C$_2$H$_4$), δ 1.25 (s C$_4$H$_8$)

$^{13}$C NMR (DMSO): δ 171.77 (s OC=O), δ 117.81 (t CF$_2$), δ 114.15-114.86 (t CF$_2$), δ 105.46-112.92 (m CF$_2$), δ 58.55-59.26 (t CH$_2$O), δ 32.87 (s C$\underline{H}_2$C=O), δ 28.10-28.34 (m C$_2$H$_4$), δ 24.10 (s C$_2$H$_4$)

$^{19}$F NMR (DMSO): δ −50.20−−50.17 (s 4F), δ −64.40−−64.36 (s 4F)

IR: 1756 cm$^{-1}$ (OC=O), 1108 cm$^{-1}$ (C—F)

TGA: One mass loss is seen giving a boiling range of 330-350° C.

Density: 1.28 g/ml
Viscosity: 26.33 cP

| RPM | Centipoise (cP) | Torque (%) |
|---|---|---|
| 2 | Out of Range | Out of Range |
| 3 | 25.4 | 12.7 |
| 4 | 25.6 | 17.1 |
| 5 | 25.7 | 21.4 |
| 6 | 25.7 | 25.7 |
| 10 | 26.09 | 43.5 |
| 12 | 26.09 | 52.2 |
| 20 | 26.33 | 87.8 |
| 30 | Out of Range | Out of Range |

Synthesis of 1:1 Combination of Compounds of Formula (V) and (VI)

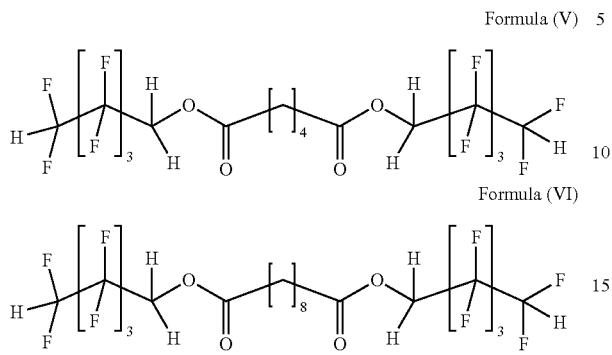

Formula (V)

Formula (VI)

Sebacoyl chloride (32.66 g, 0.14 mol) and adipoyl chloride (25.00 g, 0.14 mol) were charged to a 250 mL round bottom flask fitted with a condenser and dropping funnel. The acid chloride mixture was stirred at room temperature. 1H, 1H, 5H-Octafluoropentan-1-ol (133.31 g, 0.55 mol) was charged to a dropping funnel and added slowly to the mixture. The mixture was stirred at 40° C. for approximately 7 hours, allowed to cool to room temperature and then the reaction mixture was worked up. The remaining clear oil was filtered to remove particulates and then dried over activated molecular sieves. The reaction gave 123 g of compounds of Formula (V) and (VI).

$^1$H NMR (DMSO): δ 6.85-7.23 (tt, CF$_2$H), δ 4.73-4.83 (t CH$_2$), δ 2.38-2.47 (m C$_2$H$_4$), δ 1.51-1.59 (m C$_2$H$_4$), δ 1.24 (s C$_4$H$_8$)

$^{13}$C NMR (DMSO): δ 171.54 (s OC=O), δ 171.32 (s OC=O), δ 118.06-117.65 (m CF$_2$), δ 115.09-113.53 (m CF$_2$), δ 111.59-110.05 (m CF$_2$), δ 109.64-107.45 (m CF$_2$), δ 104.11-104.92 (m CF$_2$) δ 58.16-58.86 (m CH$_2$O), δ 32.39-33.13 (s x2 CH$_2$C=O), δ 28.01-28.27 (d C$_2$H$_4$), δ24.07 (s C$_2$H$_4$), δ 23.32 (s C$_2$H$_4$)

$^{19}$F NMR (DMSO): δ-43.64--43.54 (s 4F), δ-49.62--49.37 (s 4F), δ-54.46--54.19 (s 4F), δ-63.09--62.90 (s 4F)

IR: 1759 cm$^{-1}$ (OC=O), 1126 cm$^{-1}$ (C—F)

TGA: One mass loss is seen giving a boiling range of 320 to 365° C. No impurities Density: 1.49 g/mL Viscosity: 41.04 cP

| RPM | Centipoise (cP) | Torque (%) |
|---|---|---|
| <2 | Out of Range | Out of Range |
| 2 | 39.9 | 13.3 |
| 3 | 40.6 | 20.3 |
| 4 | 40.6 | 27.1 |
| 5 | 40.6 | 33.8 |
| 6 | 40.5 | 40.5 |
| 10 | 41.03 | 68.4 |
| 12 | 41.04 | 82.1 |
| 20 | Out of Range | Out of Range |

The individually made oils (compounds of Formula (V) and (VI)) were then mixed together in 3 different molar ratios: 1:1, 1:2 and 2:1 respectively. Viscosity and density measurements were then performed on all mixtures.

| Oil mixture | RPM | Viscosity Centipoise (cP) | Torque (%) | Density (g/ml) |
|---|---|---|---|---|
| 1:1 | 2 | 36.0 | 12.0 | 1.49 |
|  | 3 | 36.6 | 18.3 |  |
|  | 4 | 36.4 | 24.3 |  |
|  | 5 | 36.6 | 30.5 |  |
|  | 6 | 36.9 | 36.9 |  |
|  | 10 | 37.12 | 62.0 |  |
|  | 12 | 37.74 | 74.7 |  |
| 1:2 | 2 | 35.4 | 11.8 | 1.47 |
|  | 3 | 37.2 | 18.6 |  |
|  | 4 | 36.9 | 24.6 |  |
|  | 5 | 37.2 | 31.0 |  |
|  | 6 | 37.3 | 37.3 |  |
|  | 10 | 37.37 | 62.3 |  |
|  | 12 | 37.19 | 74.4 |  |
| 2:1 | 2 | 35.4 | 11.8 | 1.51 |
|  | 3 | 35.8 | 17.9 |  |
|  | 4 | 37.0 | 24.7 |  |
|  | 5 | 36.6 | 30.5 |  |
|  | 6 | 37.0 | 37.0 |  |
|  | 10 | 37.13 | 61.9 |  |
|  | 12 | 37.19 | 74.4 |  |

Flammability

Selected fluorinated fluids of the invention were tested to assess their flammability and/or combustibility alone and mixed with fluorocarbon refrigerant compositions. It was found that the fluorinated species exhibited elevated combustion temperature compared to commercially available polyalkylene glycol (PAG) and polyol ester (POE) lubricant materials.

Experimental Method—Hot Manifold Testing

An assessment was made of the ease of ignition of the fluids when in contact with a hot metal surface, using the test apparatus and test method as described in ISO Standard ISO 20823:2003. In this test droplets of the fluid were allowed to fall vertically downwards onto an internally heated, cylindrical hot surface, inclined at a shallow angle to the horizontal, and which was additionally fitted with a horizontal gutter to trap liquid at one side of the cylindrical body. (The surface is hereinafter described as the "manifold").

The temperature of the manifold was increased stepwise until ignition was observed. Observations on the character and vigour of ignition were also recorded during each test. Five fluids of the invention, two PAG type lubricants (Nippon Denso ND12 and Daphne FD46XG) and one POE lubricant (Emkarate RL68H) were tested. A perfluorinated lubricant material (DuPont Krytox™ GPL150) was also tested as a comparative example. The results are tabulated below:

| Fluid | Highest temperature without ignition (° C.) | Lowest temperature with ignition (° C.) | Observations |
|---|---|---|---|
| Formula (V) | 633 | 643 | Immediate ignition |
| Formula (VI) | 608 | 615 | Immediate ignition |
| Formula (VII) | 604 | 615 | Immediate |
| Compound of formula (IV) | 626 | 635 | 30 s delay before ignition |
| 2:1 Combination of compounds of Formula (V) and (VI) | 636 | 643 | 28 s delay before ignition |
| ND12 (PAG) | 438 | 443 | Immediate ignition; burning liquid collected |
| FD46XG (PAG) | 462 | 467 | Immediate ignition; burning liquid collected |

| Fluid | Highest temperature without ignition (° C.) | Lowest temperature with ignition (° C.) | Observations |
|---|---|---|---|
| RL68H (POE) | 628 | 633 | Immediate ignition; gas above tray also ignited by droplets |
| Krytox GPL150 | 770 | None observed in range 600-770° C. | Smoke but no flame |

It is evident that the fluids of the invention require significantly higher surface temperatures to initiate combustion than those of the PAG fluids. Two of the fluids tested also have ignition temperatures comparable or higher to that of the POE fluid tested. Both of these fluids exhibit significantly delayed and less vigorous combustion than the POE fluid.

Experimental Method—Testing in Refrigerant Mixtures

The combustion behaviour of mixtures of one of the fluids of the invention (2:1 combination of compounds of Formula (V) and (VI)) with the refrigerant fluid 2,3,3,3-tetrafluoropropene (R-1234yf) when in contact with a hot metal surface was investigated. Refrigerant R1234yf is proposed as a suitable fluid for automotive air-conditioning systems, where a leak from the system could result in a spray of refrigerant/oil mixture contacting hot engine surfaces.

The apparatus used comprised an enclosed cubical test chamber, 30 cm on a side, with transparent side and front faces and steel back, top and bottom faces. The two side faces were hinged to provide a means of pressure relief in the event of an ignition.

A horizontal, hollow, steel cylinder with closed front face, diameter ca 75 mm and length ca 70 mm, was mounted onto the steel back face of the chamber with its centre point approximately 160 mm above the base plate. This cylinder was heated on its inside surfaces from outside the test cell by using an oxy-acetylene torch whose flame jet was aimed into the cylinder. Thermocouples were spot-welded into the top and bottom of the cylinder and the heating torch gas rates were adjusted until the temperatures indicated on each thermocouple were steady and within 10 K of each other. Additional thermocouples were used to monitor the air temperature at top, middle and bottom of the test chamber. Once the hot surface was at steady state, a liquid mixture of refrigerant and lubricant was injected to the test chamber, using a short pipe section of Swagelok tubing (6 mm external diameter) as an injection point. The tube was centrally mounted in the base of the test chamber and protruded about 10 mm into the test chamber. This resulted in a vertical spray of droplets and vaporised refrigerant entering the chamber, where its momentum ensured rapid mixing into the chamber atmosphere. A sketch of the test cell is shown in FIG. 1 to illustrate the geometry used.

For each experiment a constant quantity (~20 grams) of the refrigerant/oil mixture was placed in a feed reservoir vessel, isolated from the chamber by a solenoid valve and initially at lab ambient temperature (typically from 18 to 20° C.). A standard concentration of 3% by weight oil in refrigerant was used. This is typical of the oil content in refrigerant circulating in automotive air conditioning systems.

Video cameras were used to film the release and any subsequent ignition events. When the solenoid valve was opened the pressure inside the feed cylinder was monitored as an indication of whether the release had finished. The apparatus was monitored for 5 minutes after each injection for evidence of flame (visual and by observing the thermocouple readings). After each injection event an air purge was used to flush the feed lines and the test chamber before the next injection.

The temperature of the hot surface was progressively increased until an ignition event was observed. For each temperature where no ignition was observed at least one repeat test was carried out as a check on reproducibility.

It was found that the highest hot surface temperature at which no ignition was observed was 818° C. for the combination of R-1234yf with the combination of compounds of Formula (V) and (VI) fluid. The lowest temperature at which ignition was observed was 822° C.

A comparative test was made using R-1234yf with PAG lubricant ND12 (a lubricant intended for use with R-1234yf refrigerant). It was found that the highest hot surface temperature at which no ignition was observed with this mixture was 795° C. The lowest temperature at which ignition was observed was 802° C.

The fluorinated fluid of the invention thus retarded the onset of ignition in this test as compared to the PAG fluid at an equal mass loading in the refrigerant.

The invention claimed is:

1. A composition comprising a heat transfer fluid and a lubricant, the lubricant comprising the two compounds of formula (V) and formula (VI):

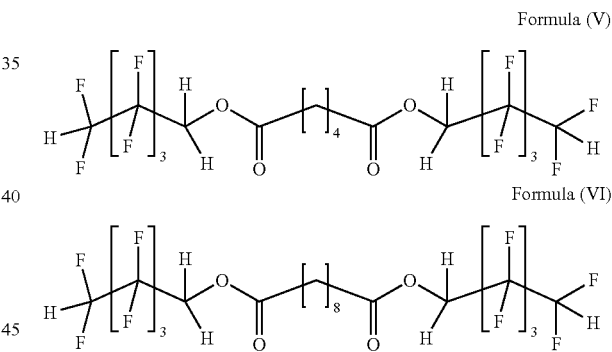

wherein the two compounds of formula (V) and formula (VI) have a molar ratio in the range of 2:1 to 1:2.

2. A composition according to claim 1 wherein the two compounds of formula (V) and formula (VI) have a 2:1 molar ratio.

3. A composition according to claim 1 wherein the two compounds of formula (V) and formula (VI) have a 1:1 molar ratio.

4. A composition according to claim 1 wherein the two compounds of formula (V) and formula (VI) have a 1:2 molar ratio.

5. A composition according to claim 1 wherein the heat transfer fluid is selected from the group consisting of (hydro)fluoroolefins (HFOs), hydrofluorocarbons (HFCs), chlorofluorocarbons (CFCs), hydrochlorofluorocarbons (HCFCs), hydrocarbons, and combinations thereof, or
   wherein the heat transfer fluid is selected from the group consisting of R-1234ze, R-1234yf, R-1233xf, R-1233zd, R-1243zf, R-134a, R-152a, R-32, R-161, R-125, R-134, propane, propylene, carbon dioxide, R-245fa, R-236fa, R-227ea, R-143a, n-butane, isobutane, R-365mfc, and combinations thereof, optionally wherein the heat transfer fluid is selected from the group consisting of R-1234ze, R-1234yf, R-1233xf, R-1233zd, R-1243zf, R-134a, R-152a, R-32, and combinations thereof, or wherein the heat transfer fluid comprises R-1234ze or R-1234yf.

6. A composition according to claim 1, which is less flammable than a composition comprising the same heat transfer fluid combined with a polyalkylene glycol (PAG) and/or polyol ester (POE) based lubricant, or which has an ignition temperature of about 500° C. or greater, or which is non-flammable.

7. A composition according to claim 1 further comprising a stabiliser, optionally the stabiliser is selected from the group consisting of diene-based compounds, phosphates, phenol compounds and epoxides, and mixtures thereof, optionally further comprising a flame retardant, and optionally the flame retardant is selected from the group consisting of tri-(2-chloroethyl)-phosphate, (chloropropyl) phosphate, tri-(2,3-dibromopropyl)-phosphate, tri-(1,3-dichloropropyl)-phosphate, diammonium phosphate, various halogenated aromatic compounds, antimony oxide, aluminium trihydrate, polyvinyl chloride, a fluorinated iodocarbon, a fluorinated bromocarbon, trifluoro iodomethane, perfluoroalkyl amines, bromo-fluoroalkyl amines and mixtures thereof.

8. A heat transfer device containing a composition as defined in claim 1.

9. A heat transfer device according to claim 8, which is a refrigeration device.

10. A heat transfer device according to claim 9, which is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems, the heat transfer device optionally further containing a compressor.

11. A method of reducing the flammability of a composition by the addition of the composition of claim 1.

* * * * *